(12) United States Patent
Lin

(10) Patent No.: US 6,210,414 B1
(45) Date of Patent: Apr. 3, 2001

(54) BONE FASTENER FOR SHINBONE AND THIGHBONE

(76) Inventor: Chin Lin, Department of Orthpaedic Surgery National Taiwan University Hospital No. 7, Chung S. Road, Taipei (TW)

( * ) Notice: Subject to any disclaimer, the term of this patent is extended or adjusted under 35 U.S.C. 154(b) by 0 days.

(21) Appl. No.: 09/553,321

(22) Filed: Apr. 20, 2000

(51) Int. Cl.[7] .................................................. A61B 17/72
(52) U.S. Cl. .................................................. 606/64; 606/62
(58) Field of Search .................................................. 606/62, 63, 64, 606/67, 68, 72, 73

(56) References Cited

U.S. PATENT DOCUMENTS

| | | | |
|---|---|---|---|
| 4,827,914 | * | 5/1989 | Brumfield . |
| 5,472,444 | * | 12/1995 | Huebner et al. .................................................. 606/64 |
| 5,779,705 | * | 7/1998 | Matthews .................................................. 606/67 |

\* cited by examiner

*Primary Examiner*—David O. Reip
(74) *Attorney, Agent, or Firm*—Shoemaker and Mattare, Ltd.

(57) ABSTRACT

A new type of bone fastener is proposed, which is suitable for implantation either in a fractured shinbone (tibia) or a fractured thighbone (femur). The bone fastener includes an elongated steel tube having a bent tail portion, a middle portion, and a frontal portion, with a plurality of screw holes being formed in a non-parallel manner in the bent tail portion and the frontal portion. Further, a set of bolts are selectively screwed to the screw holes depending on the case of either a shinbone fracture or a thighbone fracture so as to secure the fractured part together. Since the screw holes and the bolts are oriented in a non-parallel manner, the bone fastener can be hardly loosened off position when the user moves on foot at fast paces, thus providing a better fastening effect than the prior art.

8 Claims, 3 Drawing Sheets

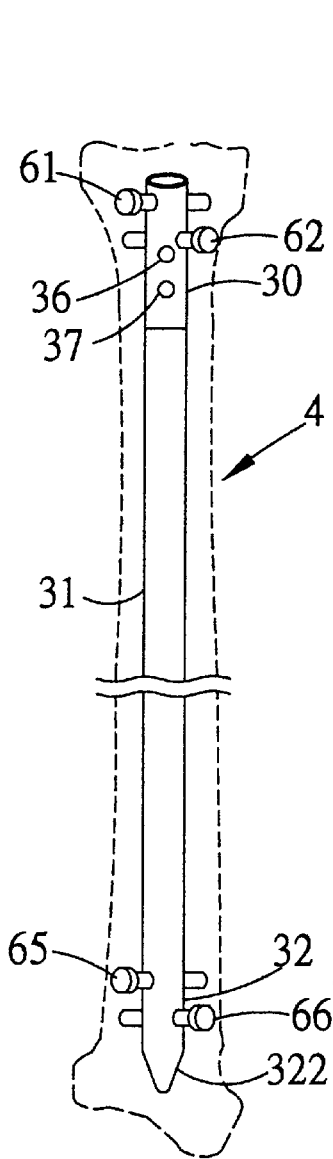
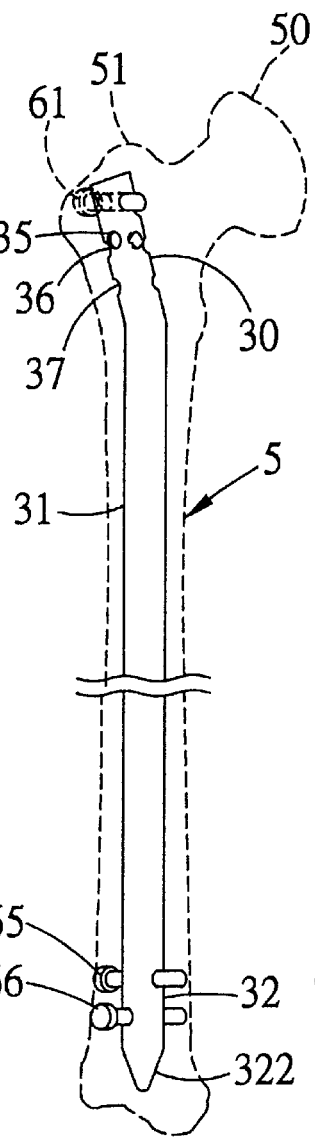
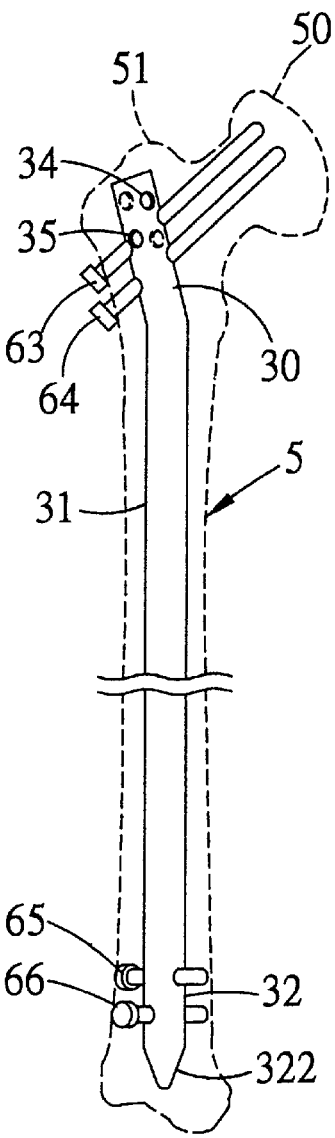

BONE FASTENER FOR SHINBONE AND THIGHBONE

BACKGROUND OF THE INVENTION

1. Field of the Invention

This invention relates to a new type of bone fastener that is suited for implantation either in a fractured shinbone (tibia) or a fractured thighbone (femur).

2. Description of Related Art

FIGS. 7 and 8 are schematic diagrams showing the implantation of a conventional shinbone fastener 1 in a shinbone 4. As shown, the shinbone fastener 1 is an elongated steel tube having a bent tail portion 10, a middle portion 11, and a frontal portion 12. The bent tail portion 10 is formed with a pair of screw holes 131, 132, and the frontal portion 12 is also formed with a pair of screw holes 133, 134. The longitudinal axis 101 of the bent tail portion 10 is angled with respect to the longitudinal axis 111 of the middle portion 11 by a predetermined angle. This angled design is required to allow the shinbone fastener 1 to be easily inserted from the top end 41 of the shinbone 4 to the inside of the shinbone 4.

As shown in FIG. 8, when the shinbone fastener 1 is implanted in position in the shinbone 4 (i.e., when the frontal portion 12 reaches the bottom end of the shinbone 4), bolts 14, 15, 16, 17 are screwed into the screw holes 131, 132, 133, 134 respectively so as to secure the shinbone fastener 1 firmly in position in the shinbone 4.

When the bolts 14, 15, 16, 17 are screwed in position, they are substantially parallel to each other since all the screw holes 131, 132, 133, 134 are oriented substantially in perpendicular to the longitudinal axis of the shinbone 4. One drawback to this design, however, is that when the user moves on foot at fast paces, it can cause the bolts 14, 15, 16, 17 to be easily loosened off position and thus cause injury to the shinbone 4.

FIGS. 9 and 10 are schematic diagrams showing the implantation of a conventional thighbone fastener 2 in a thighbone 5. As shown, the thighbone fastener 2 is also an elongated steel tube having a bent tail portion 20 formed with a pair of screw holes 21, 22 which are oriented in an angled manner with respect to the longitudinal axis of the thighbone 5. As illustrated in FIG. 9, when the neck part 50 of the thighbone 5 suffers from fracture, a pair of elongated bolts 24, 25 can be screwed respectively into the screw holes 21, 22 so as to fastened the fractured neck part firmly together. Furthermore, a third screw hole 26 is formed near the top end of the thighbone fastener 2. As illustrated in FIG. 10, when the main part of the thighbone 5 suffers from fracture, an elongated bolt 27 can be screwed into the screw hole 26 so as to fastened the fractured part firmly together.

One drawback to the forgoing bone fasteners, however, is that they are suited only to one kind of bone, i.e., either to the shinbone or to the thighbone, but not both, which makes the use of them quite cost-ineffective. There exists therefore a need for a new type of bone fastener that is suitable for use in shinbone and thighbone.

SUMMARY OF THE INVENTION

It is therefore an objective of this invention to provide a new type of bone fastener, which is suitable for use either on a fractured shinbone or a fractured thighbone.

It is another objective of this invention to provide a new type of bone fastener, which can provide a better fastening effect than the prior art so that it would not be loosened off position when the user moves on foot at fast paces.

It is still another objective of this invention to provide a new type of bone fastener, which can be more cost-effective to manufacture.

In accordance with the foregoing and other objectives, the invention proposes a new type of bone fastener. The bone fastener of the invention comprises: (a) an elongated steel tube having a bent tail portion, a middle portion linked to the bent tail portion, and a frontal portion; the bent tail portion being angled by a predetermined angle with respect to the middle portion, and the bent tail portion and the middle portion together defining a plane which divides the steel tube into a first part and a second part; the bent tail portion being formed with a first screw hole, a second screw hole, a third screw hole, and a fourth screw hole; the first screw hole extending from the first part to the second part of the steel tube, and the second screw hole extending from the second part to the first part of the steel tube and is oriented perpendicularly with respect to the first screw hole; the third screw hole and the fourth screw hole being parallel to each other and oriented to the plane; the frontal portion being formed with a fifth screw hole and a sixth screw hole oriented in perpendicular to the fifth screw hole; and (b) a plurality of bolts selectively screwed to the first, second, third, fourth, fifth, and six screw holes depending on the case of either a shinbone fracture or a thighbone fracture.

In the foregoing bone fastener of the invention, since the screw holes and the bolts are oriented in a non-parallel manner, the proposed bone fastener can be hardly loosened off position when the user moves on foot at fast paces, thus providing a better fastening effect than the prior art.

BRIEF DESCRIPTION OF DRAWINGS

The invention can be more fully understood by reading the following detailed description of the preferred embodiments, with reference made to the accompanying drawings, wherein:

FIG. 4 is a schematic diagram showing the implantation of the bone fastener of the invention in a shinbone;

FIG. 5 is a schematic diagram showing a first example of the implantation of the bone fastener of the invention in a thighbone;

FIG. 6 is a schematic diagram showing a second example of the implantation of the bone fastener of the invention in a thighbone;

DETAILED DESCRIPTION OF PREFERRED EMBODIMENTS

Figure 1:
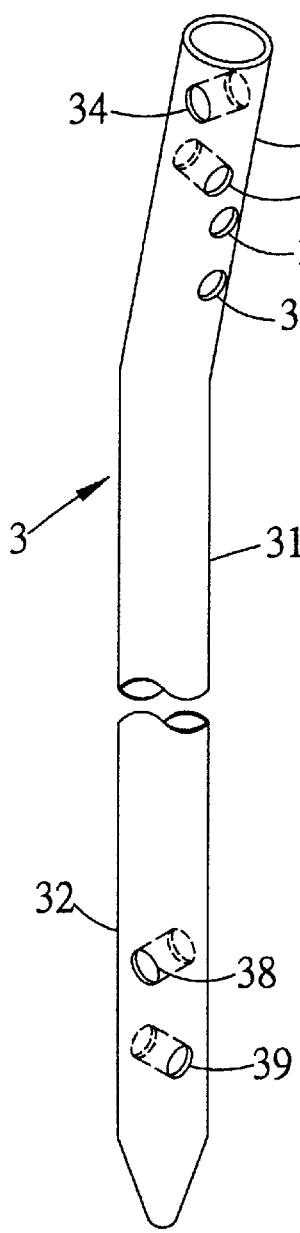
FIG. 1 is a schematic perspective view of the bone fastener of the invention.
Figure 2:
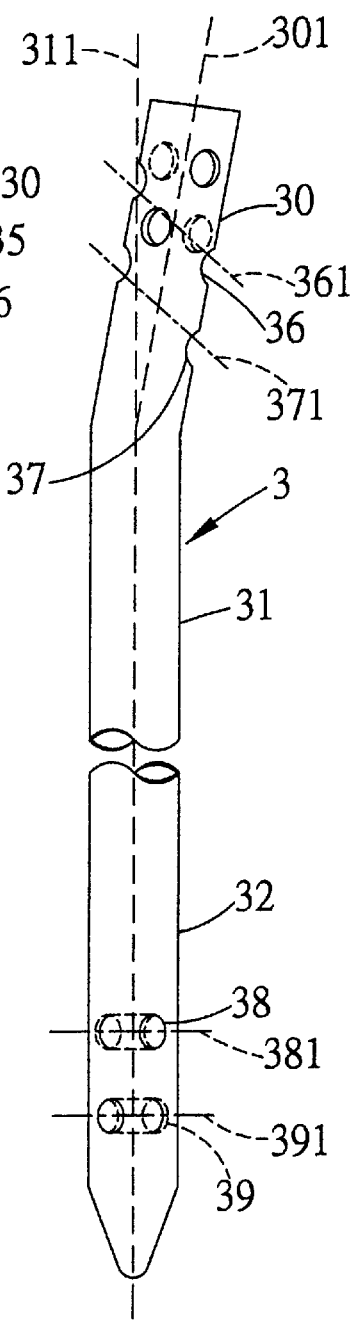
FIG. 2 shows a schematic longitudinal sectional view of the bone fastener of the invention.
Figure 3:
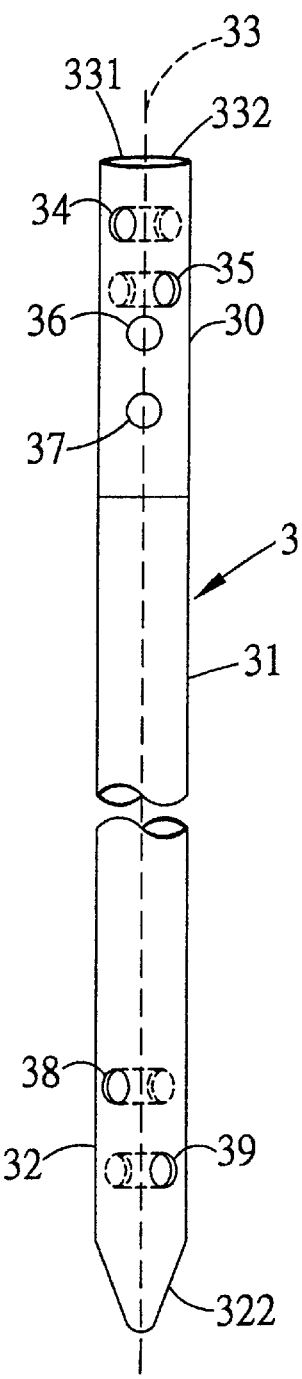
FIG. 3 shows another schematic longitudinal sectional view of the bone fastener of the invention.
Figures 7, 8, 9, 10:
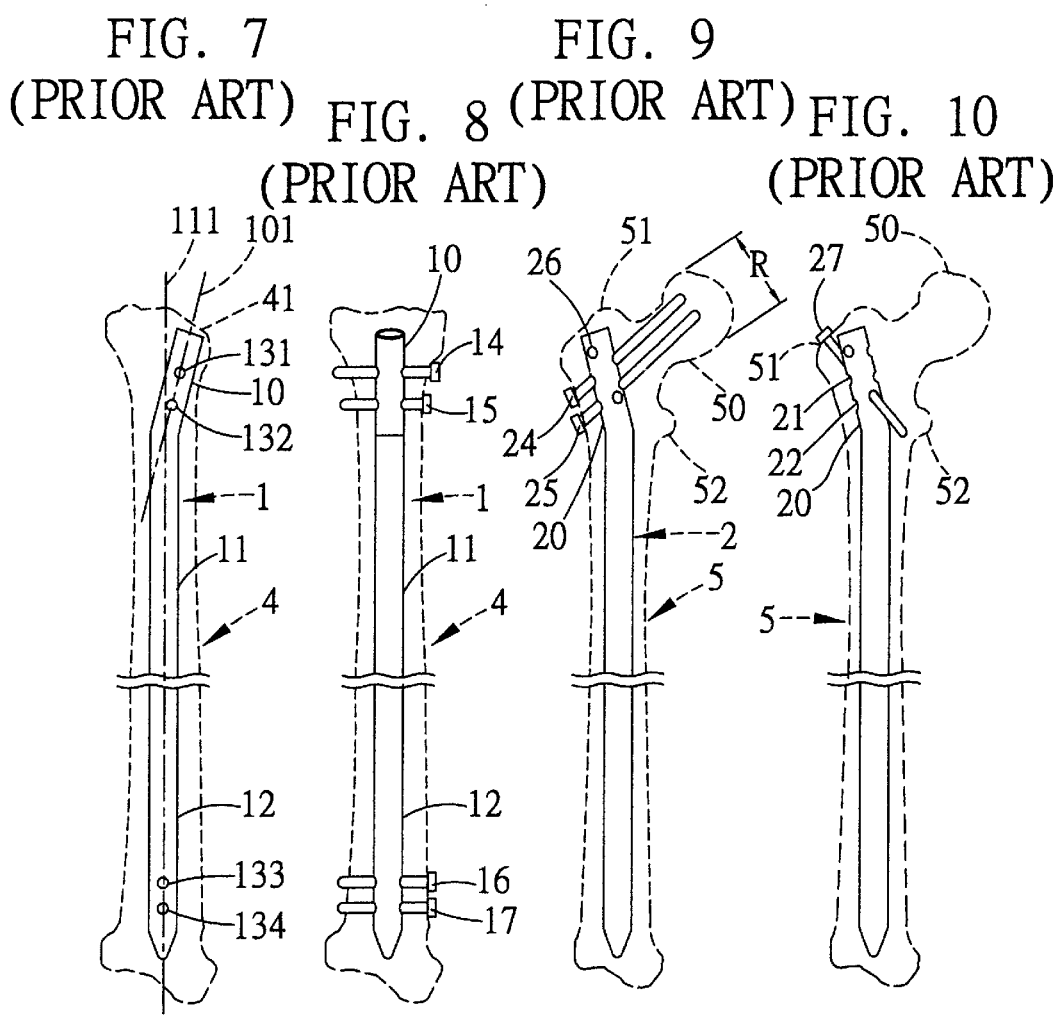
FIG. 7 (PRIOR ART) is a schematic diagram showing the implantation of a conventional shinbone fastener.
FIG. 8 (PRIOR ART) is a schematic diagram showing another longitudinal sectional view of the shinbone fastener of FIG. 7.
FIG. 9 (PRIOR ART) is a schematic diagram showing the implantation of a conventional thighbone fastener.
FIG. 10 (PRIOR ART) is a schematic diagram showing another longitudinal sectional view of the thighbone fastener of FIG. 9.

Referring to FIGS. 1–3, the bone fastener of the invention is an elongated steel tube 3 having a bent tail portion 30, a middle portion 31, and a frontal portion 32.

The longitudinal axis 301 of the bent tail portion 30 is angled with respect to the longitudinal axis 311 of the middle portion 31 by a predetermined angle, preferably from 3° to 15°, and more preferably from 4° to 10°. The longitudinal axis 301 of the bent tail portion 30 and the longitudinal axis 311 of the middle portion 31 define a plane 33 which divides the steel tube 3 into two parts: a first part 331 and a second part 332. The bent tail portion 30 is formed with a first screw hole 34 and a second screw hole 35, wherein the first screw hole 34 extends from the first part 331 to the second part 332 of the steel tube 3, while the second screw hole 35 extends from the second part 332 to the first part 331 of the steel tube 3 and is oriented perpendicularly with respect to the first screw hole 34. In addition, the bent tail portion 30 is formed with a third screw hole 36 and a fourth screw hole 37, which are parallel to each other and oriented to the plane 33. Further, the frontal portion 32 is formed with a fifth screw hole 38 and a sixth screw hole 39 oriented in perpendicular to the fifth screw hole 38.

The frontal portion 32 has a pointed end 322 which allows the bone fastener of the invention to be easily inserted into a shinbone or a thighbone. The cross section of the steel tube 3 can be either circular, polygonal, or pentagonal in shape.

FIG. 4 is a schematic diagram showing the implantation of the bone fastener of the invention in a shinbone 4. As shown, when the bone fastener of the invention is inserted in position within the marrow portion of the shinbone 4, the pointed end 322 of the frontal portion 32 is positioned at the ankle portion 41 beneath the shinbone 4. After this, a first bolt 61 and a second bolt 62 are respectively screwed into the first screw hole 34 and the second screw hole 35, while a fifth bolt 65 and a sixth bolt 66 are respectively screwed into the fifth screw hole 38 and the sixth screw hole 39, whereby the bone fastener of the invention can be securely firmly in position in the shinbone 4.

When screwed in position, the first bolt 61 and the second bolt 62 are oriented in perpendicular to each other and to the longitudinal axis 301 of the bent tail portion 30, and the first bolt 61 extends from the first part 331 to the second part 332 of the steel tube 3, while the second bolt 62 extends from the second part 332 to the first part 331 of the steel tube 3. Since the first bolt 61 and the second bolt 62 screwed to the bent tail portion 30 are oriented in a non-parallel manner, and similarly the fifth bolt 65 and the sixth bolt 66 screwed to the frontal portion 32 are oriented in a non-parallel manner, the bone fastener of the invention can be hardly loosened off position when the user moves on foot at fast paces. The invention therefore can provide a better fastening effect than the prior art when implanted in shinbone.

FIGS. 5 and 6 are schematic diagrams showing two examples of the implantation of the bone fastener of the invention in a thighbone 5; wherein FIG. 5 shows the use of the bone fastener of the invention in the case of a fracture beyond the neck portion 50 of the thighbone 5, whereas FIG. 6 shows the use of the bone fastener of the invention in the case of a fracture in the neck portion 50 of the thighbone 5.

As shown in FIG. 5, in the case of a fracture beyond the neck portion 50 of the thighbone 5, the bone fastener of the invention is inserted through the curved portion 51 of the thighbone 5 into the marrow portion of the thighbone 5; and after the bone fastener of the invention is inserted in position, a first bolt 61 is screwed into the first screw hole 34, while a fifth bolt 65 and a sixth bolt 66 are respectively screwed into the fifth screw hole 38 and the sixth screw hole 39, whereby the bone fastener of the invention can be securely firmly in position in the thighbone 5. Optionally, a second bolt 62 can be additionally screwed into the second screw hole 35 to provide a more strengthened fastening effect.

On the other hand, as shown in FIG. 6, in the case of a fracture in the neck portion 50 of the thighbone 5, a third bolt 63 and a fourth bolt 64 are respectively screwed into the third screw hole 36 and the fourth screw hole 37, whereby the bone fastener of the invention can be securely firmly in position in the thighbone 5. When screwed in position, the third bolt 63 and the fourth bolt 64 are abutted firmly on the neck portion 50 of the thighbone 5, so that they can help secure the fracture in the neck portion 50 of the thighbone 5.

In conclusion, the invention provides a new bone fastener that can be used for implantation in either a fractured shinbone or a fractured thighbone to help secure the fracture therein. It can be learned from the foregoing description that the bone fastener of the invention can provide a better fastening effect than the prior art; and therefore, the invention is more advantageous to use than the prior art.

The invention has been described using exemplary preferred embodiments. However, it is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

What is claimed is:

1. A bone fastener, which is suited for implantation either in a fractured shinbone or a fractured thighbone, and which comprises:
   (a) an elongated steel tube having a bent tail portion, a middle portion linked to the bent tail portion, and a frontal portion; the bent tail portion being angled by a predetermined angle with respect to the middle portion, and the bent tail portion and the middle portion together defining a plane which divides the steel tube into a first part and a second part; the bent tail portion being formed with a first screw hole, a second screw hole, a third screw hole, and a fourth screw hole; the first screw hole extending from the first part to the second part of the steel tube, and the second screw hole extending from the second part to the first part of the steel tube and is oriented perpendicularly with respect to the first screw hole; the third screw hole and the fourth screw hole being parallel to each other and oriented to the plane; the frontal portion being formed with a fifth screw hole and a sixth screw hole oriented in perpendicular to the fifth screw hole; and
   (b) a plurality of bolts selectively screwed to the first, second, third, fourth, fifth, and six screw holes depending on the case of either a shinbone fracture or a thighbone fracture.

2. The bone fastener of claim 1, wherein the frontal portion has a pointed end.

3. The bone fastener of claim 1, wherein the predetermined angle between the bent tail portion and the middle portion is from 3° to 15°.

4. The bone fastener of claim 3, wherein the predetermined angle between the bent tail portion and the middle portion is from 4° to 10°.

5. The bone fastener of claim 1, wherein in the case of a shinbone fracture, a first pair of bolts are screwed respectively to the first screw hole and the second screw hole in the bent tail portion, while a second pair of bolts are screwed respectively to the fifth screw hole and the sixth screw hole in the frontal portion.

6. The bone fastener of claim 1, wherein in the case of a thighbone fracture beyond a neck portion of the thighbone, a first bolt is screwed into the first screw hole, while a pair of bolts are respectively screwed into the fifth screw hole and the sixth screw hole.

7. The bone fastener of claim 6, wherein in the thighbone fracture case, an additional bolt is screwed into the second screw hole.

8. The bone fastener of claim 1, wherein in the case of a thighbone fracture in a neck portion of the thighbone, a first pair of bolts are respectively screwed into the third screw hole and the fourth screw hole in the bent tail portion, and a second pair of bolts are respectively screwed into the fifth screw hole and the sixth screw hole in the bent tail portion.

* * * * *